United States Patent
Mizutani

(10) Patent No.: US 6,616,644 B1
(45) Date of Patent: Sep. 9, 2003

(54) SANITARY NAPKIN

(75) Inventor: Satoshi Mizutani, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/427,921

(22) Filed: Oct. 27, 1999

(30) Foreign Application Priority Data

Oct. 30, 1998 (JP) .......................... 10-309926

(51) Int. Cl.[7] .............................................. A61F 13/15
(52) U.S. Cl. ............................ 604/385.04; 604/385.28
(58) Field of Search ........................ 604/358, 385.01, 604/385.03, 385.04, 385.24, 385.25, 386, 387, 389, 390, 385.28

(56) References Cited

U.S. PATENT DOCUMENTS 5,752,947 A * 5/1998 Awolin ..................... 604/387
5,921,975 A * 7/1999 Suzuki et al. ............ 604/385.2

FOREIGN PATENT DOCUMENTS

| GB | 2 296 445 A | 7/1996 |
|---|---|---|
| GB | 2 329 842 A | 4/1999 |
| JP | A-6-125938 | 5/1994 |
| WO | WO95/08972 | 4/1995 |
| WO | WO97/43994 | 11/1997 |
| WO | WO98/31320 | 7/1998 |

OTHER PUBLICATIONS

Copy of European Search Report mailed Aug. 30, 2001.

* cited by examiner

Primary Examiner—Weilun Lo
Assistant Examiner—Jamisue Webb
(74) Attorney, Agent, or Firm—Butzel Long

(57) ABSTRACT

A sanitary napkin provided on its upper surface along transversely opposite side portions with a pair of barrier flaps, respectively. Each of the barrier straps are stretchable outward transversely of the napkin and so that a wearer's thighs and peripheral edges of an undergarment adjacent leg-openings are protected from being soiled with body liquids.

12 Claims, 5 Drawing Sheets

SANITARY NAPKIN

BACKGROUND OF THE INVENTION

This invention relates to a sanitary napkin and the like for absorption and containment of body fluids.

Japanese Patent Application Disclosure Gazette (Kokai) No. Hei6-125938 discloses a sanitary napkin including a pair of lateral edges projecting outward along transversely opposite sides of a liquid-absorbent pad. With the napkin fastened to a crotch region of an undergarment worn by a wearer, the lateral edges extend on the inner surface of the undergarment beyond peripheral edges of its leg-openings so that the lateral edges may cover the peripheral edges of the leg-openings and at the same time may be placed against the wearer's thighs.

With the known napkin, the lateral edges function to prevent the leg-openings' peripheral edges of the undergarment from being soiled with menstrual discharge. It is also possible for the napkin to prevent menstrual discharge from leaking down through gaps between the leg-openings' peripheral edges of the undergarment and the wearer's thighs in the course of wearing the undergarment to which the napkin has been fastened. However, the known napkin must be configured in a relatively large size so that the lateral edges may project beyond the leg-openings' peripheral edges of the undergarment. In consequence, complicated sequence of folding the individual napkins for packaging them one by one is required before they are supplied consumers and the individually packaged napkins are inevitably bulky.

SUMMARY OF THE INVENTION

It is an object of the present invention to provide a sanitary napkin which protects the leg-openings' peripheral edges of undergarment worn by a wearer from being soiled with body fluids such as menstrual discharge and protects body fluids from leaking down through gaps between the leg-openings' peripheral edges and the wearer's thighs while the napkin is configured in a relatively small size.

According to the present invention, there is provided a sanitary napkin comprising a base member and a pair of barrier flaps, the base member including a liquid-pervious topsheet, a liquid-impervious backsheet, a liquid-absorbent core disposed between the topsheet and the backsheet, a pair of transversely opposite outer side portions extending in a longitudinal direction and a pair of longitudinally opposite end portions extending in transverse direction of the napkin, and the pair of barrier flaps being formed on an upper surface of the base member's outer side portions so as to extend along the outer side portions between the pair of end portions.

Each of the barrier flaps has a fixed edge portion and a free edge portion, both extending in the longitudinal direction, and a pair of longitudinally opposite end portions between the fixed and free edge portions, the free edge portion is stretchable outward transversely of the base member and the fixed edge portion is fixed on an upper surface of the base member along the outer side portion thereof with the free edge portion pointing outward transversely of the base member.

According to one embodiment of the present invention, the free edge portion of the barrier flaps is stretchable outward at least over a partial dimension thereof in the longitudinal direction beyond the corresponding outer side portion of the base member.

According to another embodiment of the present invention, the free edge portion of the barrier flaps is stretchable outward beyond the corresponding outer side portion of the base member by 10 mm or more.

According to still another embodiment of the present invention, each of the barrier flaps is folded back on itself along a folding line extending in the longitudinal direction of the base member so as to divide the barrier flaps in the fixed edge portion and the free edge portion so that the free edge portion point outward in the transverse direction of the base member.

According to further another embodiment of the present invention, each of the barrier flaps is formed from a sheet material that is elastically stretchable in the transverse direction of the base member.

According to an additional embodiment of the present invention, each of the barrier flaps has a plurality of pleats extending in parallel one to another in the longitudinal direction of the base member and is stretchable outward in the transverse direction of the base member.

According to still additional embodiment of the present invention, each of the barrier flaps presents a static friction factor of 0.3 or higher at least on a part of a surface thereof.

According to further additional embodiment of the present invention, each of the barrier flaps is formed from a sheet material that is elastically stretchable in the longitudinal direction of the base member.

DETAILED DESCRIPTION OF THE PREFERRED EMBODIMENTS

Details of a sanitary napkin according to the present invention will be more fully understood from the description given hereunder with reference to the accompanying drawings.

Figure 1:
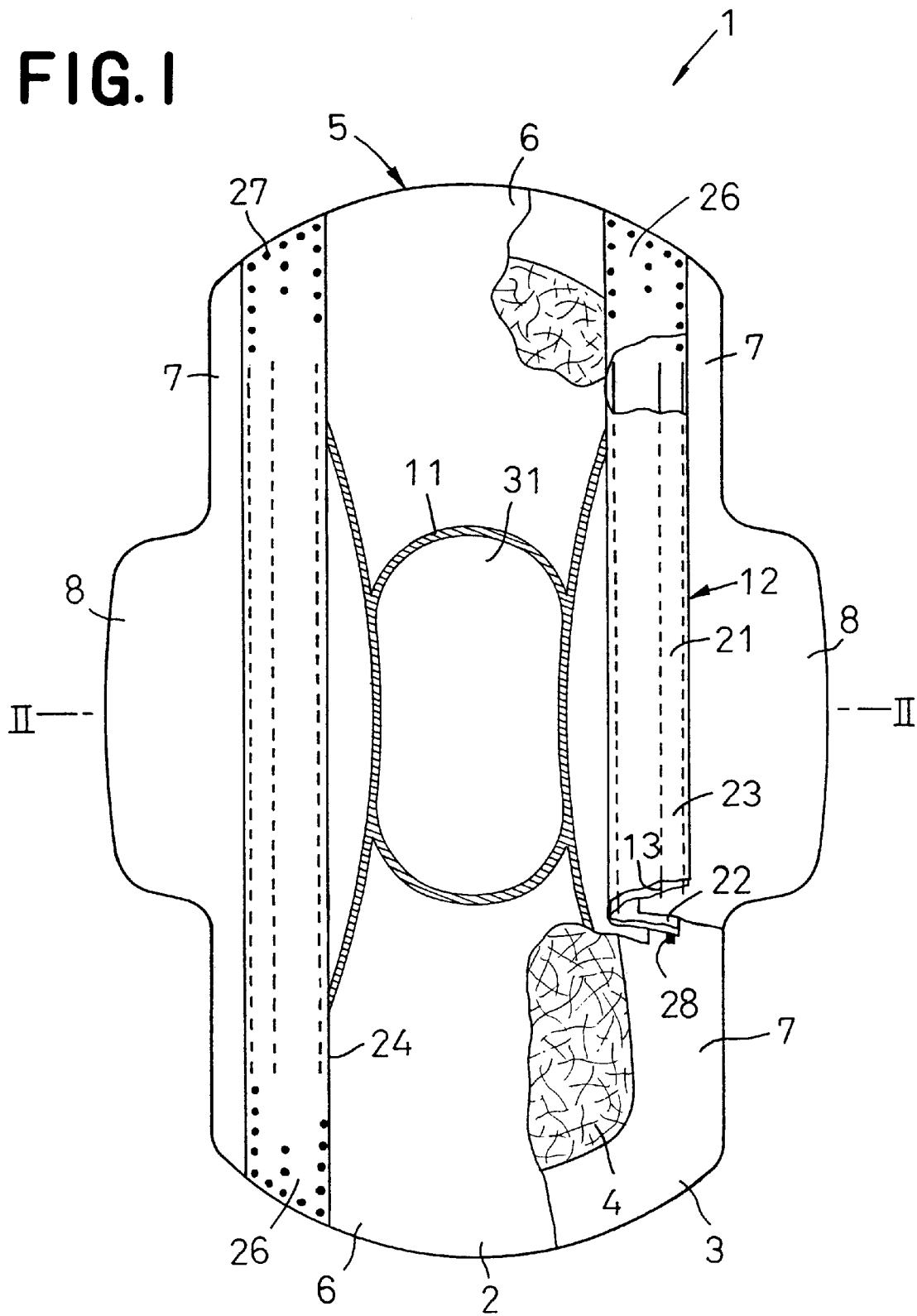
FIG. 1 is a plan view showing a partially cutaway sanitary napkin according to an embodiment of the present invention.
Figure 2:
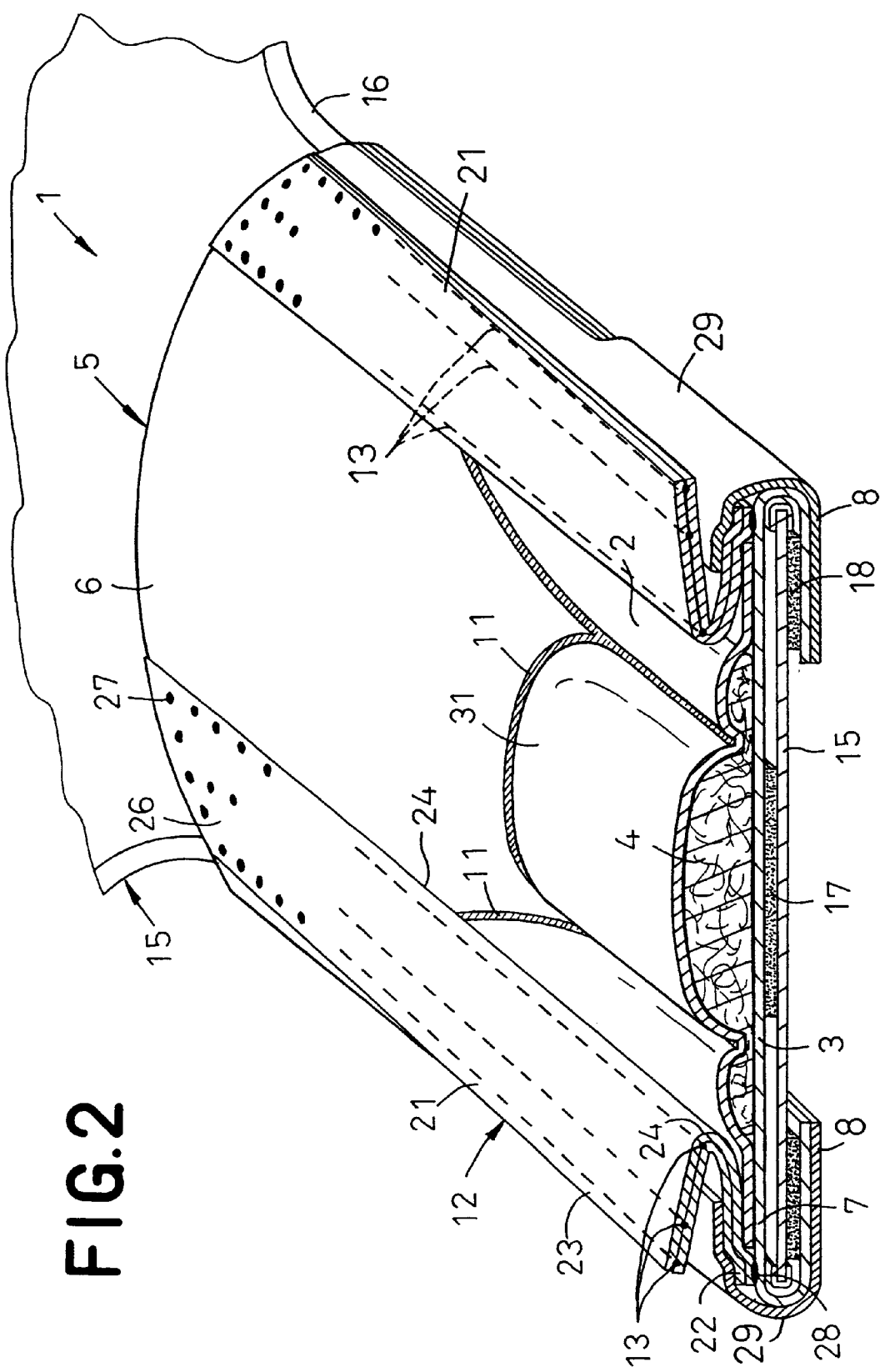
FIG. 2 is a perspective view showing the same napkin partially in a section taken along a line II—II in FIG. 1 as fastened to an undergarment worn by a napkin wearer.

FIG. 1 is a plan view showing a partially cutaway sanitary napkin 1 and FIG. 2 is a fragmentary perspective view showing the napkin 1 partially in a section taken along a line II—II in FIG. 1 as fastened to an undergarment worn by a napkin wearer. The napkin 1 comprises a base member 5 being larger in its longitudinal direction and a pair of barrier flaps 12 attached to the base member 5.

The base member 5 includes a liquid-pervious topsheet 2, a liquid-impervious backsheet 3 and a liquid-absorbent core 4 disposed between these two sheets 2, 3. The topsheet 2 and the backsheet 3 are placed upon and bonded to each other along portions which extend outward beyond a peripheral edge of the core 4 so as to form a pair of longitudinally opposed and transversely extending ends 6 and a pair of transversely opposed and longitudinally extending outer side portions 7. A pair of wings 8 extend laterally from longitudinally middle zones of the respective outer side portions 7, respectively. In a longitudinally and transversely middle zone of the base member 5, the topsheet 2 is compressed toward the core 4 to form a groove 11 on the inner surface of the base member 5. In addition, the base member 5 is provided along its transversely opposite side portions with the pair of barrier flaps 12 extending longitudinally of the base member 5, respectively. The barrier flaps 12 are provided with elastic members 13 longitudinally extending and bonded to the barrier flaps 12 under tension.

Each of the barrier flaps 12 comprises a pair of longitudinally larger sheets 21, preferably liquid-impervious sheets 21, more preferably liquid-impervious sheets 21 having an elasticity in the transverse direction of the napkin 1. The two sheets 21 are placed upon and bonded to each other by means of hot melt adhesive (not shown) to form a fixed edge portion 22 and a free edge portion 23 extending in parallel to each other longitudinally of the base member 5 and longitudinally opposite fixed edge portions 26, 26 extending in parallel to each other transversely of the base member 5. Each of the barrier flaps 12 is folded in two along a folding line 24 lying between the fixed edge portion 22 and the free edge portion 23 and extending in parallel to the edge portions 22, 23 so that the free edge portion 23 may point outwardly of the napkin 1. The fixed edge portions 26 of the barrier flaps 12 are bonded to the inner surface of the base member 5 along its outer side portions 7 by means of hot melt adhesive 28 and the fixed end portions 26 of the barrier flaps 12 are bonded to the longitudinally opposite end portions 6 of the base member 5 by means of heat-sealing zones 27. The elastic members 13 are disposed between the respective pairs of sheets 21 constituting the barrier flaps 12 so as to extend longitudinally of the barrier flaps 12 and secured under tension to the inner surface of at least one of these two sheets 21 by means of hot melt adhesive (not shown). In the vicinity of the outer side portions 7 of the base member 5, the backsheet 3 extends outward beyond the side edges of the topsheet 2 and the fixed edge portions 22 of the respective barrier flaps 12 are bonded to the upper surface of the backsheet 3 along its portion extending outward beyond the side edges of the topsheet 2 by means of hot melt adhesive 28. The fixed edge portions 22 and the portions of the backsheet 3 lying outside the fixed edge portions 22 have their upper surfaces covered with hem sheets 29 made of a hydrophobic nonwoven fabric such as a melt blown nonwoven fabric having a soft touch and forming the wings 8.

As shown in FIG. 2, the napkin 1 is fastened to a sanitary undergarment 15 in a manner as will be described. The napkin 1 is separably fastened to the inner surface of the undergarment crotch region by means of adhesive agent (not shown) applied on the outer surface of the backsheet 3 on its transversely middle zone. In order to ensure that the napkin 1 can be more reliably fastened to the undergarment 15, the wings 8 are folded along respective peripheral edges of leg-openings of the undergarment 15 and are separably fastened to the outer surface of the undergarment 15 by means of adhesive agent (not shown) applied on the outer surface of the wings 8. As the napkin 1 fastened to the undergarment 15 is curved longitudinally thereof, contraction of the elastic members 13 causes the free edges 23 of the respective barrier flaps 12 to rise above the inner surface of the base member 5 along its outer side portions 7.

A central zone 31 of the napkin 1 surrounded by the groove 11 is significantly protuberant relatively to its surrounding zone, as will be apparent from FIG. 2, and therefore can be placed against a wearer' vaginal orifice under good fitting.

Figure 3:
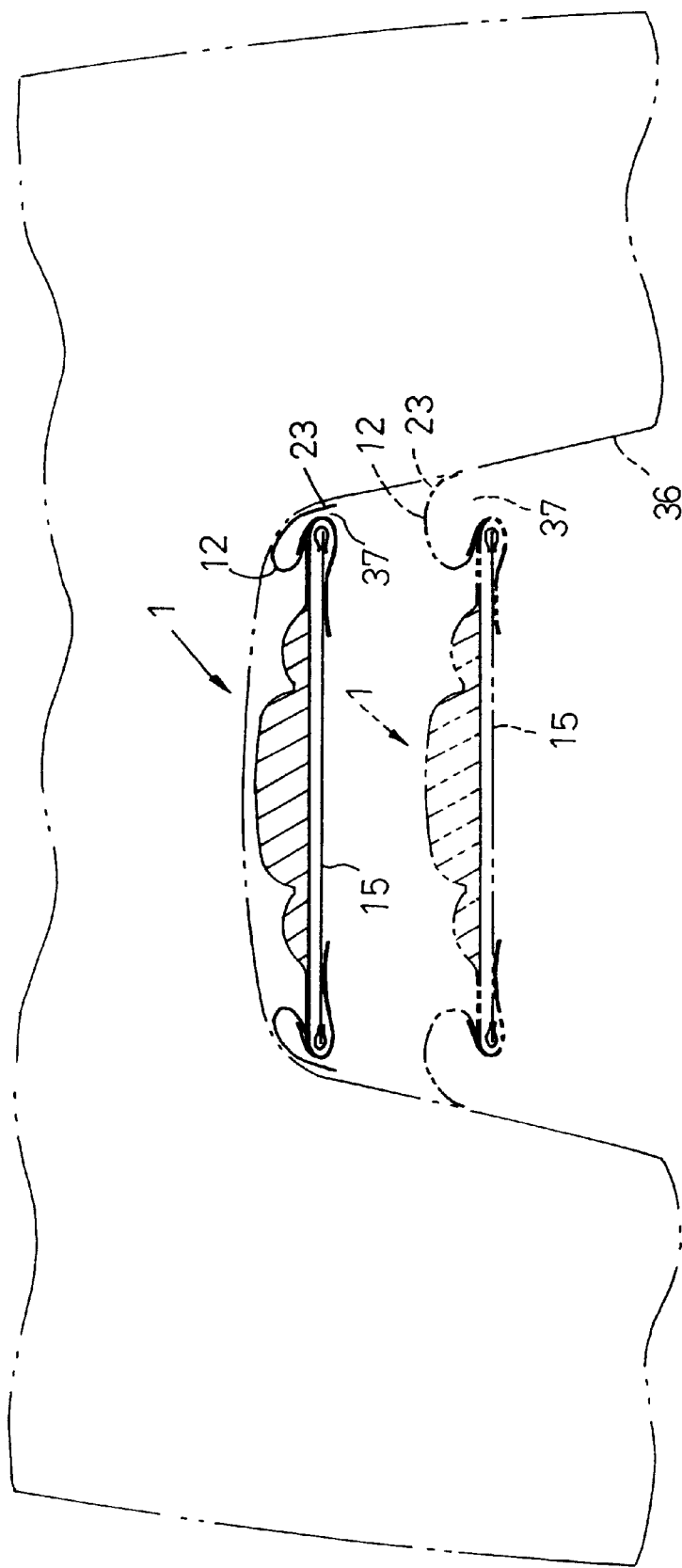
FIG. 3 is a sectional view showing the same napkin as put on the wearer's body.

FIG. 3 is a schematic diagram illustrating a section taken transversely of the napkin 1, in which the napkin 1 fastened to the undergarment 15 is indicated by solid lines, the napkin 1 in the course of being fastened to the undergarment 15 is indicated by imaginary lines and a crotch region of the wearer inclusive of her thighs 36 is also indicated by imaginary lines. As the undergarment 15 are lifted around the thighs 36, the free edge portions 23 of the respective barrier flaps 12 rub the thighs 36 and thereupon the barrier flaps 12 each folded in two are unfolded and laterally smoothed to enlarge the width of the napkin 1 and to close gaps 37 between the thighs 36 and the leg-openings' peripheral edges of the undergarment 15. Such operation of the barrier flaps 12 makes it possible to prevent menstrual fluid from flowing down through the gaps 37 in the course of wearing the napkin 1 and thereby to eliminate any apprehension that the wearer's thighs 36 as well as the undergarment 15 such as the undergarment 15 might be soiled with menstrual fluid.

Figure 4:
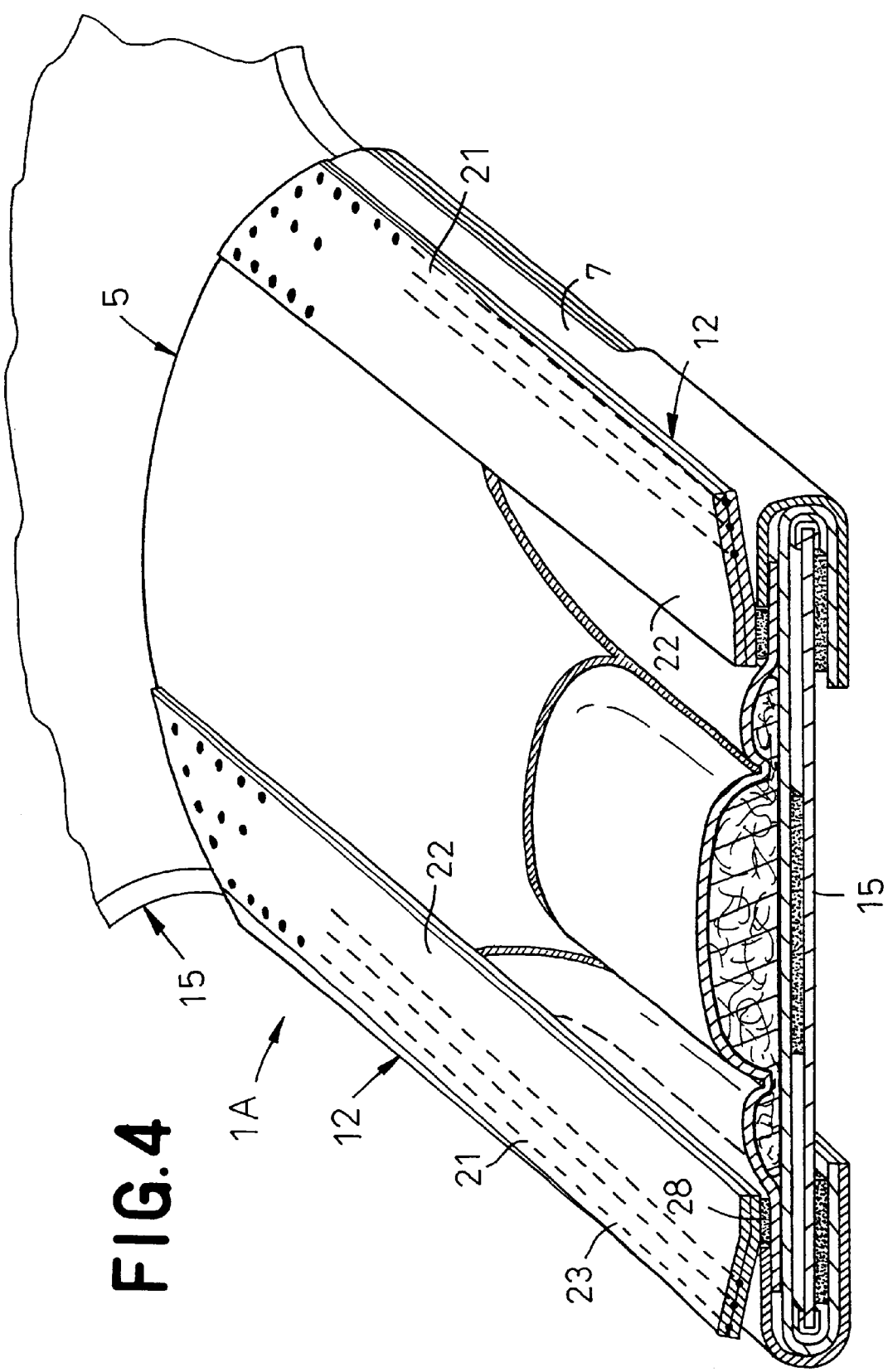
FIG. 4 is a view similar to FIG. 2, showing a napkin according to another embodiment of the present invention.

FIG. 4 is a view similar to FIG. 2, showing a napkin 1A according to another embodiment of the present invention. In the case of the napkin 1A, the barrier flaps 12 are formed by sheets 21, preferably liquid-impervious sheets 21 which are elastically stretchable and contractible transversely of the napkin 1A. The fixed edge portions 22 of the barrier flaps 12 are bonded by means of adhesive 28 to the inner surface of the base member 5 along relatively inner zones of the base member 5. The free edge portions 23 of the barrier flaps 21 extend outward relatively to the fixed edge portions 22, more preferably in the vicinity of the outermost edges of the side edge portions 7. In the course of wearing this napkin 1, the barrier flaps 12 are elastically stretched transversely of the napkin 1 as the free edge portions 23 of the respective barrier flaps 12 rub the wearer's thighs, and the barrier flaps 12 thus stretched function to close the gaps 37 between the wearer's thighs 36 and the leg-openings' peripheral edges of the undergarment.

Figure 5:
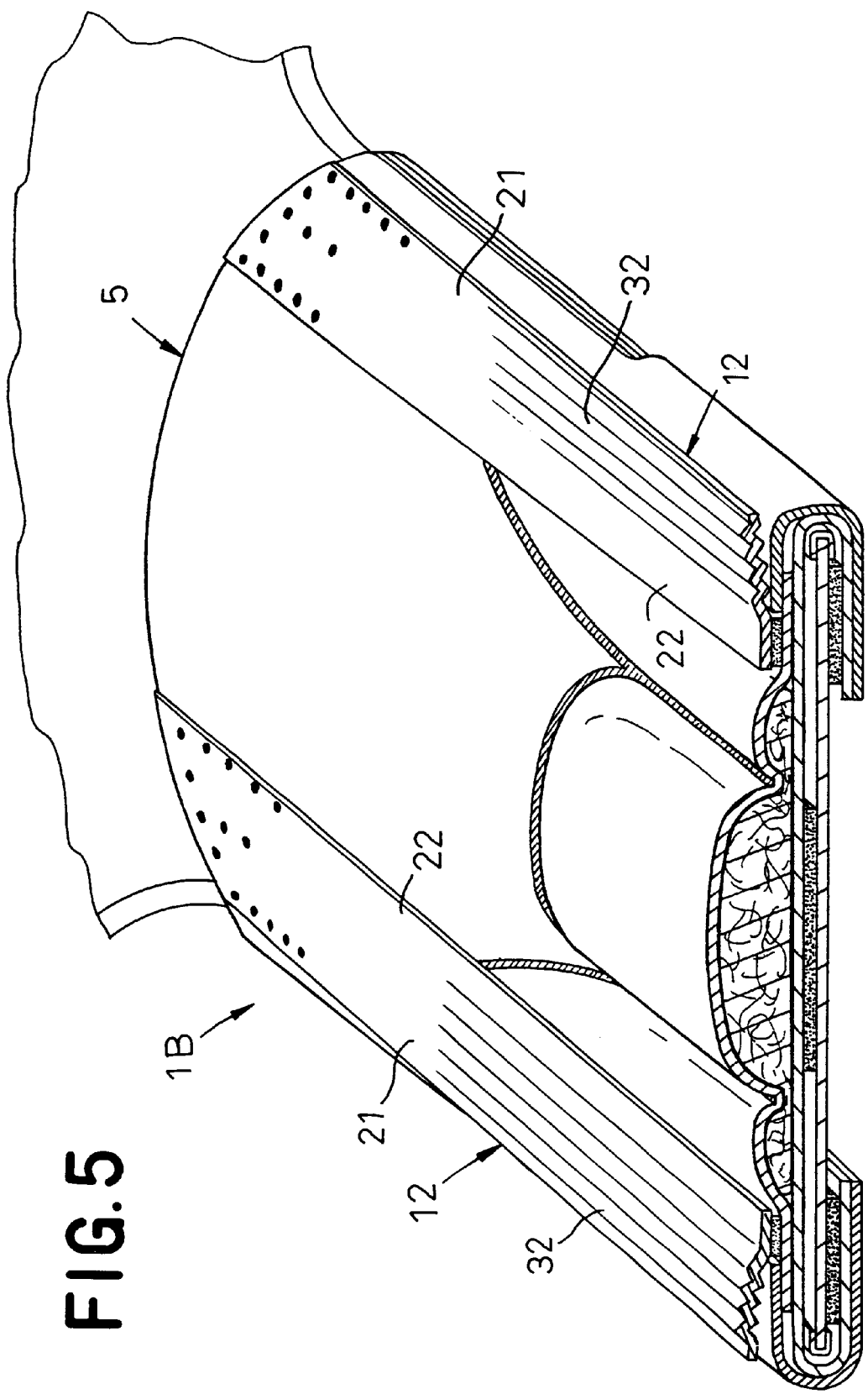
FIG. 5 is a view similar to FIG. 4, showing a sanitary napkin according to still another embodiment of the present invention.

FIG. 5 is a view similar to FIG. 4, showing a napkin 1B according to still another embodiment of this invention. In the case of the napkin 1, the barrier flaps 12 are formed by sheets 21 which have or have not an elasticity in the transverse direction thereof. The barrier flaps 12 are formed with a plurality of pleats 32 extending in parallel one to another longitudinally of the barrier flaps 12. The pleats 32 are smoothed down as the barrier flaps 12 rub the wearer's thighs and laterally pulled by the thighs. As a result, the barrier flaps 12 are sufficiently widened to operate in the same manner as in the barrier flaps 12 shown in FIG. 1.

To realize the present invention, the barrier flaps 12 preferably can be outward stretched, at least over a longitudinal partial dimension of its free edge portion 23, beyond the corresponding outer side portion 7 of the base member 5 by 10 mm or more. In order that the barrier flaps 12 can be easily stretched in this manner, each of the barrier flaps 12 preferably presents, at least in the vicinity of the free edge portion 23 adapted to rub the wearer's thigh 36, a static friction factor of 21 as specified by Japanese Industrial Standard (JIS)-P8147. According to the method set (JIS)-P8147 test pieces are attached to the top flat surface of a horizontal support plate and the flat bottom surface of a weight that is slide across the horizontal support plate, and a metallic wire or synthetic fiber is connected between a tensile tester and the leading edge of the weight. Next, the horizontal support plate is inclined and the coefficient of static friction is calculated as the mean force of static friction divided by the perpendicular load caused by the weigh. The barrier flaps 12, instead of utilizing the elastic members 13 as in the embodiment shown by FIG. 1, may utilize a longitudinally elastic sheet and, in this case, the elastic sheet may be bonded with a longitudinal tension to the base member 5. When the napkin 1, is fastened to the undergarment 15 and consequently curved longitudinally thereof, the free edge portions 23 of the barrier flaps 12 which are under the foregoing longitudinal tension contract. Thereupon, the free edge portions 23 rise above the outer side portions 7 of the napkin 1 and are easily stretched as the free edge portions 23 rub the wearer's thighs 36. It should be understood here that the sheets 21 having elasticity in a longitudinal direction thereof maybe used without tensioning the sheets 21 in the foregoing direction to form the barrier flaps 12. Each of the barrier flaps 12 may be formed by a single sheet 21 instead of two sheets 21 placed one upon another. While the napkin 1 according to the present invention preferably includes the pair of wings 8, the wings 8 may be eliminated without departing from the scope of this invention. It is also possible to eliminate the hem sheets 29 covering the fixed edge portions 22 of the barrier flaps 12.

Bonding of the respective members may be achieved by using suitable adhesive agent such as hot melt adhesive and, for the members made of thermoplastic synthetic resin, the bonding may be achieved by utilizing heat-sealing or ultrasonic sealing technique.

A nonwoven fabric or an apertured plastic film may be used as stock material for the topsheet 2 of the napkin 1 and fluff pulp or a mixture of fluff pulp and superabsorptive polymer particles may be used as stock material for the absorbent core 4. A nonwoven fabric, rubber sheet or plastic film made of plastic elastomer or the like may be used as stock material for the barrier flaps 12. To improve a static friction factor of the barrier flaps 12, the surfaces of the barrier flaps 12 may be coated with hot melt adhesive or the like or laminated thereon with strips of sheet presenting a relatively high friction factor.

With the napkin according to the present invention, the barrier flaps are stretchable outward in the transverse direction of the napkin and therefore the leg-openings' peripheral edges of the undergarment and the wearer's thighs can be protected from being soiled with menstrual discharge without previously dimensioning the napkin appropriately wide. Such napkin can be configured sufficiently small to be convenient for compactly packaging the individual napkin and for carrying about the individually packaged napkin.

What is claimed is:

1. A sanitary napkin comprising:
   a base member formed from a liquid-pervious topsheet, a liquid-impervious backsheet, and a liquid-absorbent core disposed between said liquid-pervious topsheet and said liquid-impervious backsheet, said base member having an upper surface, transversely opposite outer side portions extending in a longitudinal direction of said sanitary napkin and longitudinally opposite end portions extending in a transverse direction of said sanitary napkin; and
   a pair of barrier flaps formed on upper surfaces of said transversely opposite outer side portions so as to extend along said transversely opposite outer side portions between said longitudinally opposite end portions,
   each barrier flap of said pair of barrier flaps having a fixed edge portion which extends in said longitudinal direction and a free edge portion which extends in said longitudinal direction, and a pair of longitudinally opposite end portions,
   each barrier flap of said pair of barrier flaps being fixed to the upper surface of said base member only at the fixed edge portion and the longitudinally opposite end portions of the barrier flap, the opposite end portions of each barrier flap being fixed flatly against the upper surface of the base member across an entire width of each barrier flap,
   said free edge portion of each barrier flap of said pair of barrier flaps being stretchable outward transversely of said base member so as to extend outward beyond transversely opposite side edges of the base member when worn by a wearer.

2. The sanitary napkin according to claim 1, therein said free edge portion of each one of said barrier flaps is stretchable outward at least over a partial dimension thereof in said longitudinal direction beyond an adjacent one of said opposite outer side portions of said base member.

3. The sanitary napkin according to claim 2, wherein said free edge portion of each one of said barrier flaps is stretchable outward beyond an adjacent one of said opposite outer side portions of said base member by at least 10 mm.

4. The sanitary napkin according to claim 1, wherein each one of said barrier flaps is folded back on itself along a folding line which extends in said longitudinal direction of said base member so as to divide each of said barrier flaps between said fixed edge portions and said free edge portions so that said free edge portions are directed outward in said transverse direction of said base member.

5. The sanitary napkin according to claim 1, wherein said fixed edge portion of each barrier flap of said barrier flaps is fixed on an upper portion of said base member that is defined by portions of said topsheet and said backsheet at which the core is not disposed therebetween.

6. The sanitary napkin according to clam 1, wherein said free edge portion of each barrier flap of said pair of barrier flaps is stretchable outward transversely of said base member so as to extend outward beyond tersely opposite side edges of the base member along a longitudinal length of said barrier flaps that extends between the longitudinal opposite ends of the barrier flaps which opposite ends are fixed to the upper surface of the base member.

7. The sanitary napkin according to claim 1, wherein each of said barrier flaps presents a static friction factor of 0.3 of higher at least on a part of a surface thereof.

8. The sanitary napkin according to claim 7, wherein each one of said barrier flaps is formed from sheet material and is elastically stretchable in said longitudinal direction of said base member.

9. The sanitary napkin according to claim 1, wherein the liquid-impervious backsheet of said base member has substantially parallel transversely opposite side edges.

10. The sanitary napkin according to claim 9, wherein the liquid-impervious backsheet has parallel transversely opposite side edge portions at each of opposite longitudinal end portions of the sanitary napkin which opposite side edge portions of the liquid-impervious backsheet extend outwardly beyond the See edge portions of said pair of barrier flaps other than when the sanitary napkin is worn by a wearer of the sanitary napkin.

11. The sanitary napkin according to claim 1, wherein each one of said barrier flaps is formed from a sheet material that is elastically stretchable in said transverse direction of said base member.

12. The sanitary napkin according to claim 1, wherein each one of said barrier flaps has a plurality of pleats extending parallel to one another in said longitudinal direction of said base member and each of said barrier flaps is stretchable outward in said transverse direction of said base member.

* * * * *